United States Patent [19]
Freeman

[11] Patent Number: 5,392,661
[45] Date of Patent: * Feb. 28, 1995

[54] HYDROGEN MONITORING APPARATUS

[76] Inventor: H. Bruce Freeman, No. 9, 1715 27th Avenue, NE., Calgary, Alberta, Canada, T2E 7E1

[ * ] Notice: The portion of the term of this patent subsequent to Jan. 18, 2011 has been disclaimed.

[21] Appl. No.: 154,870

[22] Filed: Nov. 18, 1993

Related U.S. Application Data

[63] Continuation of Ser. No. 819,871, Jan. 13, 1992, Pat. No. 5,279,169.

[30] Foreign Application Priority Data

Jan. 28, 1991 [CA] Canada ................................ 2035105

[51] Int. Cl.$^6$ ...................... G01N 17/00; G01N 33/00
[52] U.S. Cl. .......................................... 73/866; 73/37; 73/86
[58] Field of Search ............... 73/40, 46, 49.2, 40.5 R, 73/40.7, 37, 86, 866

[56] References Cited

U.S. PATENT DOCUMENTS

| | | | |
|---|---|---|---|
| 2,886,497 | 5/1959 | Butler | 204/1 |
| 2,946,952 | 7/1960 | Marsh et al. | 324/71 |
| 3,197,698 | 7/1965 | Schaschl et al. | 324/65 |
| 3,241,056 | 3/1966 | Lawrence, Jr. | 324/33 |
| 3,357,903 | 12/1967 | Lawrence, Jr. | 204/45 |
| 3,565,769 | 2/1971 | Holden et al. | 204/1 |
| 3,669,864 | 6/1972 | Fike | 204/195 R |
| 4,020,680 | 5/1977 | Mehdizadeh et al. | 73/86 |
| 4,056,968 | 11/1977 | Winslow, Jr. | 55/158 |
| 5,279,169 | 1/1994 | Freeman | 73/866 |

Primary Examiner—Hezron E. Williams
Assistant Examiner—George M. Dombroske
Attorney, Agent, or Firm—Biebel & French

[57] ABSTRACT

An apparatus is disclosed for measuring the diffusion of hydrogen atoms from a second surface to a first surface of a ferrous metal body as a means of measuring the magnitude of corrosion occurring at the second surface. The apparatus comprises a chamber-defining member which can be sealed to the first surface of the body so as to define with the first surface a sealed chamber. The chamber-defining member is constructed of material sufficiently flexible that upon evacuation of the sealed chamber the chamber-defining member deflects toward the first surface to reduce the chamber volume. The apparatus provides a connecting means for attaching an evacuating pump which is used to evacuate substantially all of the contents of the chamber. A valve is provided to isolate the evacuated chamber from the evacuation pump so that hydrogen atoms, generated as a result of corrosion of the second surface, migrate through the body and exit the first surface within the chamber and combine to form hydrogen molecules which collect in the chamber. A vacuum gauge is provided to monitoring the decay of the vacuum in the chamber over time.

10 Claims, 3 Drawing Sheets

HYDROGEN MONITORING APPARATUS

RELATED APPLICATION

This is a continuation of application Ser. No. 07/819,871, filed Jan. 13, 1992, now U.S. Pat. No. 5,279,169.

This invention relates to monitoring the dissipation of hydrogen atoms through a body comprised of material which is permeable to atomic hydrogen, particularly to monitoring the accumulation of molecular hydrogen gas in an evacuated chamber resulting from the migration of hydrogen atoms through such a body.

A typical example of an application in which the present invention may be used is to monitor the presence and general magnitude of corrosion occurring at a surface of a ferrous metal body when exposed to a corrodent such as water as further discussed in U.S. Pat. No. 4,043,178 and U.S. Pat. No. 4,065,373.

It is well known that when ferrous metals are exposed to water and corrode that hydrogen atoms are liberated at a rate corresponding to the rate of corrosion activity as a result of the dissociation of water molecules into hydrogen atoms and hydroxyl groups. Some of these hydrogen atoms permeate and migrate through the ferrous metal body. When such atoms resurface they combine to form molecular hydrogen gas and then dissipate.

It is desirable to monitor the magnitude of corrosion occurring on the surfaces of such bodies to provide an indication of expected depletion of the corroding surface, as well as expected hydrogen blistering corrosion as discussed in U.S. Pat. No. 4,416,996, so that appropriate remedial action may be taken. Hydrogen blistering corrosion consists of hydrogen atoms diffusing through a ferrous metal body until an imperfection in the metal is reached. At this point the hydrogen atoms combine to form molecular hydrogen gas. As ferrous metals are impervious to molecular hydrogen this is a unidirectional process and results in the accumulation of pressures of several thousand psi. Upon attaining sufficient pressure the hydrogen gas causes the metal to deform forming a blister and eventually bursting.

Both the depletion of corroding surfaces and hydrogen blistering corrosion are harmful in that they result in reducing the cross section of the body thereby weakening it. Monitoring the magnitude of corrosion occurring at a surface permits preventative maintenance to be scheduled and conducted as required to maintain the structural integrity of the body.

Various systems have sought to exploit the solubility and dissipation of atomic hydrogen as a means of monitoring the corresponding magnitude of corrosion activity.

One such device uses a ferrous metal probe within which is formed a cavity. The probe is inserted through a wall of a body into a Corrodent present therein. The resulting corrosion of the surface of the probe generates hydrogen atoms. Some of these hydrogen atoms dissipate through the wall of the probe and emerge within the cavity to form hydrogen gas.

Various measurement techniques have been used to determine the rate of production of hydrogen gas. One measurement technique used in conjunction with this type of probe measures the accumulation of hydrogen gas within the cavity over time using a pressure gauge attached to the probe remote from the corrodent.

Another measurement technique used with this type of probe continuously vents the hydrogen gas from the cavity into an ionization chamber and detector sensor whose output is measured by a scalar instrument to indicate rate of flow of the hydrogen gas.

Still another measurement technique used with this type of probe continuously vents the hydrogen gas from the cavity through a capillary port into a background liquid to form discrete uniform-dimension bubbles of hydrogen gas which are counted over time to provide the rate of flow of the hydrogen gas.

The probe type of corrosion monitoring device is of limited value because:

1. Installation of the probe requires penetrating a wall of the body to be monitored in order to place the probe within the corrodent. This compromises the integrity of the body's structure which is an important consideration in many applications as discussed in U.S. Pat. No. 4,065,373. Installation is also labour-intensive and can be a potential safety risk to installers in the event the corrodent comprises pressurized, heated, volatile or radioactive material.

2. Direct monitoring of the magnitude of corrosion of the body can only be achieved if the probe is constructed of the same material as that of the body. A probe constructed of a different material may corrode in a different fashion and at a different rate. No two materials are identical. Even variations in the specifications within the same class of material during its manufacture is normal. Materials may also be non-homogeneous. These factors make an exact match of the body and probe materials very difficult.

3. Heat affected or stressed areas, as well as areas displaying surface anomalies such as mill scale and metallurgical defects, can have a very significant effect on the surface's susceptibility to corrosion. This variance in corrosion susceptibility is a function of the materials and construction techniques used in making the body as well as the body's design. Probe type corrosion monitoring devices are unable to model or duplicate such variable susceptibility to corrosion. The indirect corrosion monitoring technique used in probe type corrosion monitoring devices cannot accurately monitor the magnitude of corrosion activity occurring in such bodies.

4. The sensitivity of the pressure-measuring style of probe is a function of the rate of hydrogen gas accumulation within the cavity. This is dependant on the corroding surface area of the probe (where the migrating hydrogen atoms are generated), the interior surface area of the cavity (through which the migrating hydrogen atoms exit to form molecular hydrogen) and the volume of the cavity. Sensitivity of the pressure-measuring style of probe to the detection of hydrogen is limited in that a substantial period of time is required to accumulate a measurable volume of hydrogen gas within the fixed volume of the probe's cavity. U.S. Pat. No. 4,043,178 discusses that even in very active corrodents the pressure build-up in such probes requires up to 24 hours to reflect gas accumulations within the cavity of 85 psi. In field conditions this may take weeks.

5. Pressure readings of the pressure-measuring style of probe will fluctuate with changes in ambient temperature inside or outside the body resulting in inaccurate indications of the magnitude of corrosion activity within the body.

6. The probe style corrosion monitoring devices are relatively expensive to manufacture and install. In addition, the venting style of probe requires careful calibration and complicated installation and is relatively too delicate for use unattended in industrial field installations.

Another device, known as a hydrogen patch, is discussed in U.S. Pat. No. 4,065,373. This style of monitoring device uses a cell mounted upon, and sealed to, the diffusion side of a body being penetrated by hydrogen atoms. The cell and the body define a cavity within which hydrogen gas forms and collects as migrating hydrogen atoms surface within the cavity.

Various measurement techniques have been used to monitor the rate of production of hydrogen within the cavity of such hydrogen patches. One such technique uses a pressure gauge to measure the accumulation of hydrogen gas over time. Another measurement technique, discussed in U.S. Pat. No. 4,065,373, electrochemically converts hydrogen atoms to ions. The rate of conversion of hydrogen atoms to ions is monitored electronically to provide a measurement of the magnitude of corrosion occurring inside the monitored body.

These hydrogen patch devices are of limited value because:

1. Pressure readings from pressure-measuring hydrogen patch devices will fluctuate with changes in ambient temperature resulting in inaccurate indications of corrosion activity within the body;
2. The sensitivity of a pressure-measuring hydrogen patch device is a function of the rate of hydrogen gas accumulation within its cavity. The sensitivity of hydrogen patch devices may generally be enhanced by maximizing the monitored surface area of the body within the cavity (through which the migrating hydrogen atoms exit to form molecular hydrogen) while minimizing the volume of the cavity. The sensitivity of a pressure-measuring hydrogen patch device is limited in that a substantial period of time is required for the accumulation of a measurable volume of hydrogen within the fixed volume of the cavity. This increases an operator's reaction time in commencing corrective action to limit corrosion-induced damage.
3. Sensitivity of the electrochemical type of hydrogen patch is practically limited by the relatively fixed surface area that they monitor on the body. Such hydrogen patches are not easily adjusted to increase the surface area they monitor due to the nature of their construction.
4. The flexibility of hydrogen patch devices to adapt to irregularly shaped body surfaces is also limited by the nature of their construction.
5. The electrochemical patch cell is relatively expensive and complicated to manufacture and to install.

SUMMARY OF INVENTION

The present invention seeks to alleviate the problems associated with the various prior art devices and techniques, and, in one aspect, provides an apparatus for measuring the diffusion of hydrogen atoms through a body, from a second surface to a first surface thereof, comprising:

(a) a chamber-defining member capable of coming into sealed engagement with the first surface of the body so as to define with the first surface a sealed chamber which is spaced from the second surface of the body;

(b) evacuating means for evacuating substantially all of the contents of the chamber;

(c) valve means for isolating the chamber from the evacuation means so that hydrogen atoms present at the second surface migrate through the body and exit the first surface within the chamber and combine to form hydrogen molecules which collect in the chamber thus resulting in a decay of the vacuum in the chamber; and (d) vacuum monitoring means for monitoring the decay of the vacuum in the chamber over time.

In another aspect, the invention provides a method for measuring the diffusion of hydrogen atoms through a body, from a second surface to a first surface thereof, comprising:

(a) sealably engaging a chamber-defining member with the first surface of the body in such a way as to define with the first surface a sealed chamber spaced from the second surface of the body;

(b) evacuating substantially all of the contents of the chamber using evacuation means;

(c) isolating the chamber from the evacuation means so that hydrogen atoms which are present at the second surface of the body migrate through the body and exit the first surface within the chamber and combine to form hydrogen molecules which collect in the chamber thus resulting in a decay of the vacuum in the chamber; and (d) monitoring the decay of the vacuum in the chamber over time.

Evacuation of the chamber reduces the effect of ambient temperature inside or outside the body on the accuracy of monitoring hydrogen gas accumulation.

In a further aspect of the invention the chamber-defining member is constructed of a material which is sufficiently flexible that it deflects toward, and comes to rest upon, the first surface upon evacuation of the chamber and remains at rest upon the first surface throughout the optimal operating range of the monitoring apparatus. This has the effect of reducing the volume of the chamber, thereby increasing the sensitivity of the apparatus to the accumulation of hydrogen gas within the chamber.

The invention provides flexibility in that its sensitivity can be increased by increasing the surface area of the body to be covered by the chamber-defining member.

Another feature of the invention is that it may be located on a variety of surfaces of the body for convenience or to monitor the magnitude of corrosion occurring at particular sites known to be susceptible to corrosion.

A further feature of the invention is that installation of the invention does not compromise the structural integrity of the body which eliminates the risk of installers being exposed to the contents of the body.

A further feature of the invention is that evacuation, isolation and monitoring of the chamber can be performed at a location remote from the body permitting the body to be located beneath the surface of the ground or submersed in a liquid.

The invention provides an inexpensive, durable, and easy to install apparatus for monitoring the magnitude of corrosion occurring at a surface.

Further features of the invention will be apparent from the following description and appended claims.

BRIEF DESCRIPTION OF THE DRAWINGS

In drawings which illustrate a preferred embodiment of the invention.

DETAILED DESCRIPTION OF THE DRAWINGS

Figure 1:
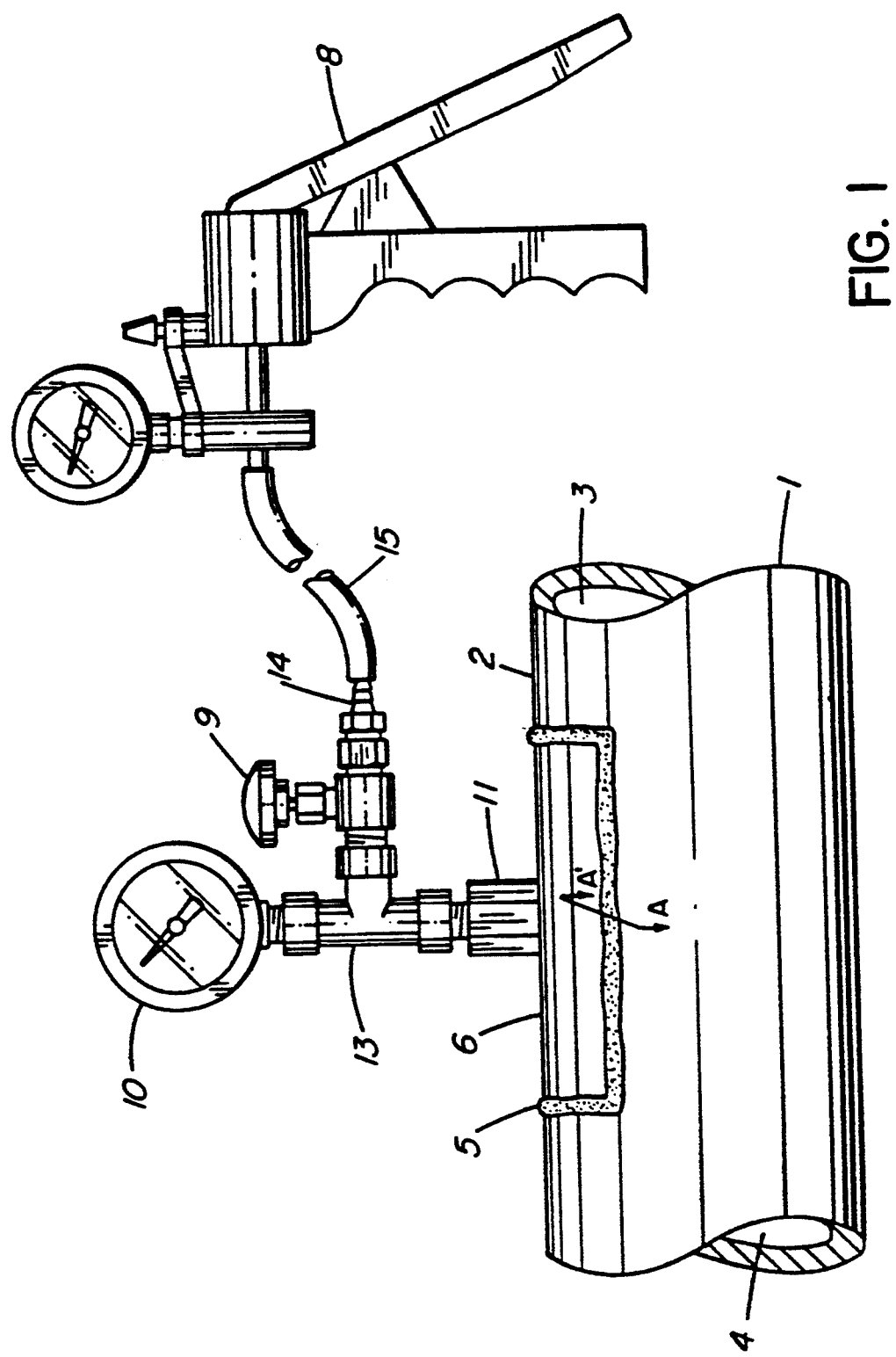
FIG. 1 illustrates a typical monitoring set-up to measure the diffusion of hydrogen atoms through a body.

Referring now to the drawings there is shown at FIG. 1 a ferrous metal body 1, defining a first surface 2 and a second surface 3. The second surface 3 is exposed to a corrosive environment 4 such as water.

Figure 3:
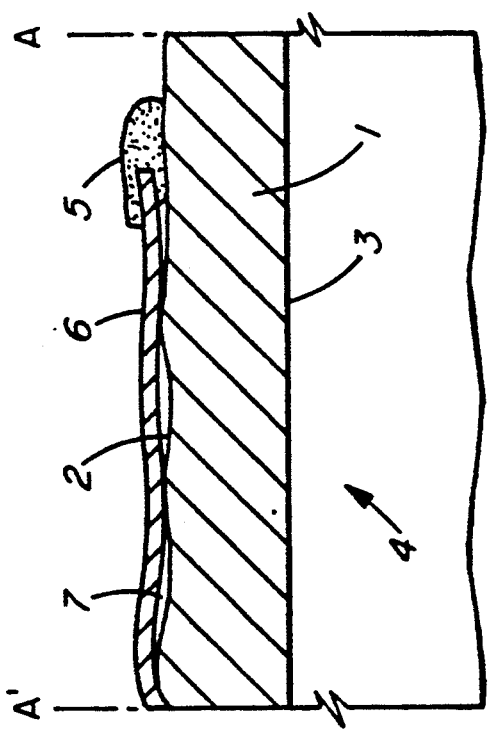
FIG. 3 is a section of FIG. 1 taken along line A—A' showing the chamber in an evacuated state.
Figure 2:
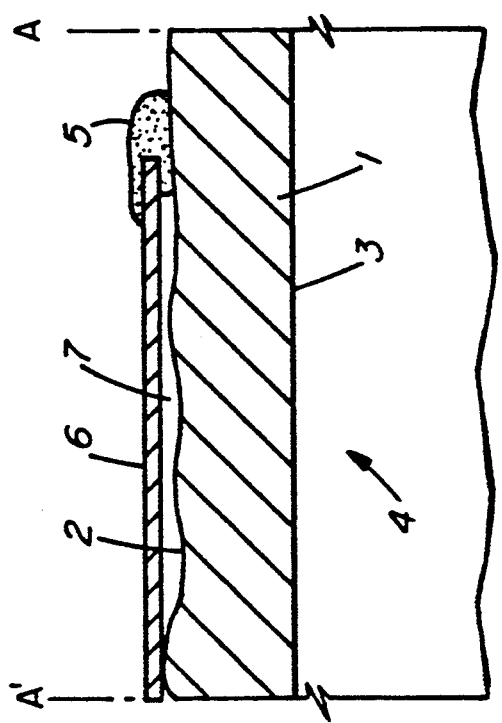
FIG. 2 is a section of FIG. 1 taken along line A—A' showing the chamber in a non-evacuated state.

A flexible chamber-defining member 6 is engaged in sealed relation with the first surface 2 to define a sealed chamber 7 spaced from the second surface 3 which is illustrated in FIG. 2 and FIG. 3 as discussed below.

A nipple 11 is attached in sealed relation with the chamber-defining member 6. The nipple 11 is connected to a three way fitting 13, the latter in turn being connected to a vacuum gauge 10 and a flow control valve 9.

The flow control valve 9 is in turn connected to a vacuum pump 8 to define a flow path from the chamber 7 to the pump 8. The valve 9 is provided to isolate the chamber 7 from the pump 8 by opening and closing the flow passage.

FIG. 2 is a section of the apparatus in FIG. 1 taken along line A—A' which indicates the position of the chamber-defining member 6 in relation to the body 1 prior to evacuation of the chamber 7. FIG. 2 illustrates a technique used to seal the chamber-defining member 6 with the first surface 2 using a surface contact adhesive 5 applied to overlap the perimeter of the chamber-defining member 6 and the first surface 2. Said perimeter may also be welded to seal the chamber-defining member 6 to the first surface 2.

As seen in FIG. 1, the chamber-defining member 6 is cut to the desired shape and size suitable to cover the area of the first surface 2 which the operator wishes to monitor. A chamber-defining member 6 having a surface area of approximately 36 square inches (a 6 inch square) has been found to be suitable for most applications. The area, shape and profile of the first surface 2 to be monitored may dictate alternative dimensions. The operator may also desire to alter the size of the chamber-defining member 6 to adjust the sensitivity of the monitoring apparatus to the accumulation of hydrogen gas. The rate of hydrogen gas accumulation in chamber 7 is directly related to the surface area of the first surface monitored. The sensitivity of the monitoring apparatus may be increased by increasing the monitored surface area of first surface. The chamber-defining member 6 may be constructed of 316 stainless steel usually between 0.004 and 0.010 inches in thickness. The reason for this preferred dimension range will become more apparent below.

The chamber-defining member 6 is prepared by altering the profile of its surface to match the corresponding profile of the first surface 2. If the body 1 comprises a pipe, the surface may be arced using a sheet metal rolling machine. A radial surface profile of the chamber-defining member 6 described by a 2 inch radius is suitable for installation on a first surface 2 having a corresponding profile described by a radius ranging from 1 inch to 6 inches. For a first surface 2 having a radial profile described by a radius greater than 6 inches, or less than 1 inch, the chamber defining member 6 must be arced accordingly.

The nipple 11 in FIG. 1 is attached in sealed relation with the chamber-defining member 6 using a soldering technique. A mandril should be used to minimize distortion of the chamber-defining member 6 during attachment of the nipple 11. For a body 1 which comprises a pipe, a mandril may be prepared from mild steel pipe approximately the same diameter as the body 1. The mandril (pipe) must be split to permit the application of heat to its interior surface. The chamber-defining member 6 is clamped tightly to the outer surface of the mandril. Hose clamps are suitable for this purpose.

A 316 stainless steel, $\frac{1}{4}$ inch male to $\frac{1}{2}$ inch female reducer nipple is suitable for most applications. The nipple 11 is prepared for engagement with the chamber-defining member 6 by using a fly cutter to curve and deburr its female end such that the engaging surface of the nipple 11 matches the profile of the engagement surface of the chamber-defining member 6 when clamped to the mandril.

With the chamber-defining member 6 clamped to the mandril, the nipple-engagement area of the chamber-defining member's outer surface is roughened. A file is suitable for this purpose. The engaging surfaces of the chamber-defining member 6 and the nipple 11 are tinned in preparation for bonding. Once tinned, the nipple 11 is placed on the chamber-defining member 6.

The interior surface of the mandril and the nipple are then simultaneously heated until the tinned surfaces of the nipple 11 and the chamber-defining member 6 fuse. This technique results in a strong bond between the nipple 11 and the chamber-defining member 6 and minimizes distortion of the chamber-defining member 6 during bonding. Once cooled, the chamber-defining member 6 may be removed from the mandril. A hole must be punctured through the chamber-defining member 6, corresponding with the centre line of the nipple 11, to establish a flow path. Care should be taken to limit distortion of the chamber-defining member 6 in puncturing said hole.

As illustrated in FIG. 1, one end of a three way fitting 13 is threaded onto the nipple 11. If remote monitoring is desired, a stainless steel capillary tube may be attached to the nipple 11. The opposite end of the capillary tube may then be attached to the three way connector. This allows the three way fitting 13 to be moved to any distance required, permitting the body 1 to be buried or submersed in liquid.

Another end of the three way fitting 13 is fitted with a vacuum gauge 10 used to monitor the decay of the vacuum in the chamber 7 over time. A conventional analogue vacuum gauge is suitable although an electronic gauge may be desired for use in conjunction with data recording and/or reporting equipment to provide a record and/or real-time reporting of vacuum decay over time.

The remaining end of the three way fitting 13 is fitted with a valve 9. A ¼ inch 316 stainless steel Marsh (trademark) or Whitney (trademark) valve is suitable. A swaged nipple 14 is threaded onto the outlet side of the valve 9 to provide a connection for a vacuum line 15 to the vacuum pump 8. When the valve 9 is in its closed position the vacuum line 15 and pump 8 may be removed if desired. Any vacuum pump 8 may be utilized which is capable of applying at least 80 Kpa of vacuum pressure and which can be transported to the monitoring location. A portable Nalgene (trademark) hand pump is suitable for most applications.

Anaerobic thread dope, teflon tape, or other suitable thread sealer is used on all threaded connections to ensure such connections are impervious to hydrogen gas.

As illustrated in FIG. 2, the chamber-defining member 6 may be attached to the first surface 2 with a surface contact adhesive 5. The chamber-defining member 6 should be cleaned of flux, grease, dirt and other surface contaminants. The surface area of the first surface 2 which is to engage the perimeter of the chamber-defining member 6 must be cleaned of all paint, corrosion and other extraneous materials so that a smooth, clean metal surface is presented. It is not necessary to clean the entire area of the first surface 2 to be covered by the chamber-defining member 6. It is sufficient to clean a strip approximately 1½ inches wide, the centerline of which corresponds to the perimeter of the chamber-defining member 6.

The chamber-defining member 6 is then placed on the intended mounting position on the first surface 2. Magnets or other suitable means, such as adhesive tape or clamps, may be used to hold the chamber-defining member 6 in position on, and in close relation to, the first surface 2.

A surface contact adhesive 5 is prepared and applied in a bead approximately ½ inch wide centred on the perimeter of the chamber-defining member 6. This bead of surface contact adhesive 5 is to approximately overlap the first surface 2 and chamber-defining member's surface opposite the chamber 7 in equal proportion (¼ inch). LePage (trademark) 5-minute epoxy has been found to be a suitable surface contact adhesive 5 for this purpose.

Vacuum may be applied to the chamber 7 to provide additional clamping force once the surface contact adhesive 5 is firm enough to withstand being drawn into the chamber 7 by the vacuum pressure.

FIG. 2 illustrates the chamber-defining member 6 at rest upon large-surface irregularities of the first surface 2 as well as on any surface contact adhesive 5 that creeps between the chamber defining member 6 and the first surface 2. In this position the volume of the unevacuated chamber 7 is defined by relatively large interstitial spaces between the points of contact of the chamber-defining member 6 and the first surface 2 or the surface contact adhesive 5.

Once the surface contact adhesive 5 has cured, monitoring may begin. Operation consists of the following steps:

1. With the valve 9 in its open position and the vacuum line 15 and pump 8 connected, evacuating the chamber until at least approximately 80 Kpa of vacuum pressure has been attained. This initial vacuum pressure value defines an acceptable upper limit of an optimal operating range of the monitoring apparatus. Higher levels of vacuum are usually not necessary. The vacuum pump 8 will evacuate substantially all of the contents of the chamber 7 which reduces the effect of ambient temperature, inside or outside the body 1, on the accuracy of monitoring the hydrogen gas accumulation.

FIG. 3 illustrates the deflection of areas of the chamber-defining member 6, not previously resting upon the first surface 2, toward the first surface 2. The preferred thickness dimension range for the chamber-defining member 6 has been discussed above. The objective in choosing the thickness of this member is to provide sufficient flexibility in the chamber-defining member 6 that areas not previously in contact with the first surface will deflect toward, and come to rest upon, the first surface 2 at a vacuum pressure substantially less than 80 Kpa, typically 10-15 Kpa, which pressure defines the lower limit of the optimal operating range of the monitoring apparatus. The choice of the appropriate thickness will depend on the shape and surface area of chamber-defining member 6 being used as well as the nature of irregularities in the surface finish of the first surface 2.

The chamber-defining member 6 remains at rest in this deflected position throughout the optimal operating range of the monitoring apparatus so that vacuum measurements are not affected by changes in the volume of the chamber 7. The chamber 7 volume throughout the optimal operating range, or fixed interstitial volume, is defined by the interstitial spaces present in the chamber 7 surrounding the surface irregularities of the first surface 2, and the surface contact adhesive 5, against which the chamber-defining member 6 has come to rest in its deflected position. The deflection of the chamber-defining member 6 in this manner serves to minimize the volume of the chamber 7 throughout the optimal operating range which results in increasing the sensitivity of the monitoring apparatus to the accumulation of hydrogen within the chamber 7.

Figure 5:
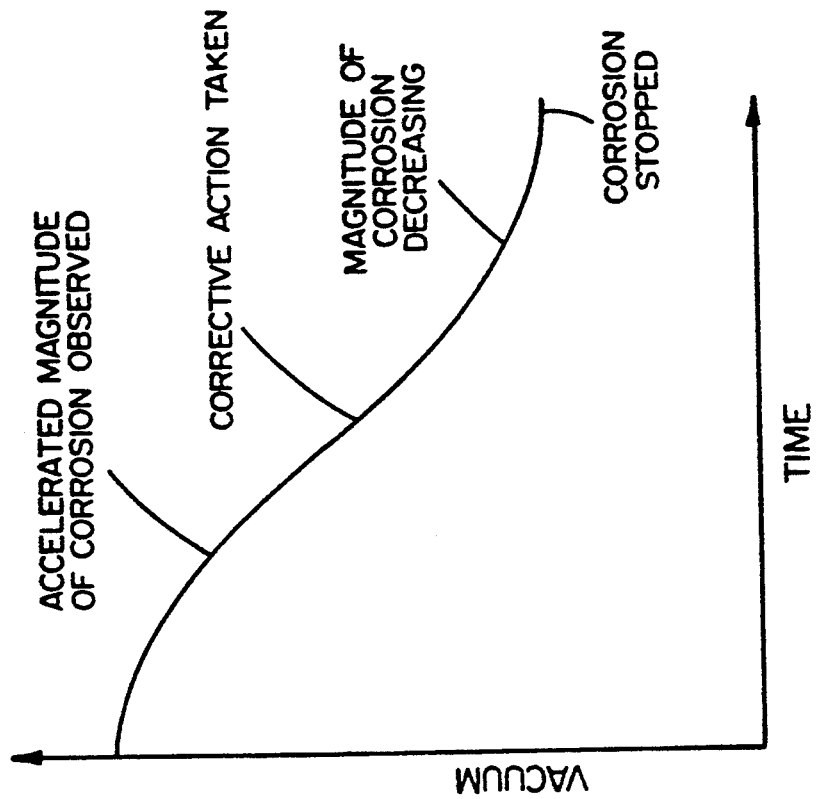
FIG. 5 is a graph (Vacuum vs Time) indicating typical vacuum decay characteristics observed using a typical monitoring apparatus when corrective action is taken to retard corrosion.
Figure 4:
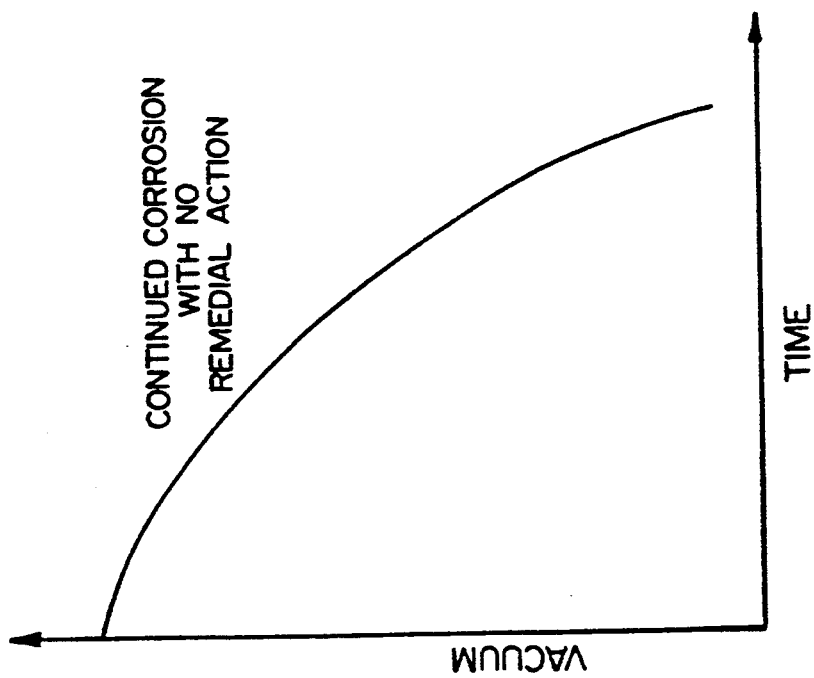
FIG. 4 is a graph (Vacuum vs Time) indicating typical vacuum decay characteristics observed using a typical monitoring apparatus when corrective action is not taken to retard corrosion.

2. Closing the valve 9.
3. Recording the initial vacuum reading.
4. Removing the vacuum pump 8 and vacuum line 15 if desired.
5. Recording the vacuum readings from the vacuum gauge 10 at regular intervals to determine the rate of accumulation of hydrogen atoms in the chamber 7. Hydrogen atoms generated as a result of corrosion of the second surface 3 will migrate through the body 1 and exit the first surface 2 within the chamber 7. These atoms will combine to form hydrogen molecules which then collect in the chamber 7 resulting in a decay of the vacuum in the chamber 7. Periodic vacuum readings will illustrate the rate of hydrogen accumulation and thereby indicate the magnitude of corrosion occurring at the second surface. The period between readings will depend on the intensity of corrosion activity at the second surface 3 and the surface area of the body 1 being monitored. Typical oil-field pipeline installations indicate that with a 36 square inch chamber-defining member 6 mounted on a body 1 experiencing active corrosion at its second surface 3, daily readings are adequate to monitor the magnitude of corrosion activity. Corrective action may be taken to retard corrosion when the indicated magnitude of corrosion activity reaches unacceptably high levels. FIG. 4 is a graph illustrating typical vacuum decay over time, measured by the monitoring apparatus, when no corrective action is taken to retard corrosion occurring at the second surface 3. FIG. 5 is a graph illustrating typical vacuum decay over time, measured by the monitoring apparatus, when corrective action has been taken to retard the rate of corrosion occurring at the second surface 3.

Since the invention disclosed herein may be embodied in other specific forms without departing from the spirit or the general characteristics thereof, some of which forms have been indicated, the embodiments described herein are considered in all respects illustrative and not restrictive. Other applications will become apparent to those skilled in the art. The scope of the invention is indicated by the appended claims, rather than by the forgoing description and all changes which come within the meaning and range of equivalency of the claims are intended to be embraced therein.

The embodiments of the invention in which an exclusive property or privilege is claimed are defined as follows:

1. A corrosion monitor for monitoring the corrosion of a non-porous steel body by measuring the diffusion of hydrogen atoms through a selected area of the body from a second surface to an opposite first surface thereof, comprising:
   (a) a chamber-defining member;
   (b) seal means extending around the marginal perimeter of the chamber-defining member for sealably securing the chamber-defining member to the first surface so as to define with said selected area of the first surface of the non-porous steel body a sealed chamber which is impervious to the flow of gas or liquid;
   (c) said chamber defining member being adapted to closely conform to the surface shape of said selected area and to lie in close proximity thereto, said chamber defining member comprising an element which is sufficiently flexible that it deflects toward, and comes to rest upon, the first surface of the body upon evacuation of the chamber so as to reduce the volume of the chamber and define a fixed interstitial volume of the chamber throughout an optimal vacuum pressure operating range;
   (d) means for connecting an evacuating means to the chamber defining member to permit substantial evacuation of the contents of the chamber to establish a partial vacuum therein;
   (e) means for isolating the chamber from the evacuation means after the partial vacuum has been established to maintain the partial vacuum in the chamber so that hydrogen atoms that are generated as a result of corrosion of the second surface of the body and which diffuse through the non-porous material of the body and which exit the first surface within the chamber and which combine to form hydrogen molecules, collect in the chamber thus resulting in a decay of the vacuum in the chamber; and
   (f) vacuum monitoring means for monitoring the decay of the vacuum in the chamber over time to give an indication of the rate of diffusion of hydrogen atoms through the selected area of the non-porous steel body and hence an indication of the rate of corrosion of said second surface.

2. A corrosion monitor as defined in claim 1, wherein the chamber-defining member is constructed of a corrosion resistant material.

3. A corrosion monitor as defined in claim 1 wherein the seal means comprises a surface contact adhesive.

4. A corrosion monitor as defined in claim 1, wherein the evacuation means, valve means and vacuum monitoring means, permit evacuation, isolation and monitoring to be conducted at a location remote from the chamber so that the corrosion monitor may be used on a body located underground or submersed in liquid.

5. A corrosion monitor as defined in claim 4, wherein the evacuation means, valve means and vacuum monitoring means, permit evacuation, isolation and monitoring to be conducted at a location remote from the chamber so that the corrosion monitor may be used on a body located underground or submersed in liquid.

6. A corrosion monitor as defined in claim 1, wherein the seal means comprises a welded seam.

7. A corrosion monitor as defined in claim 6, wherein the seal means comprises a welded seam.

8. A corrosion monitor for monitoring the corrosion of a non-porous steel body by measuring the diffusion of hydrogen atoms through a selected area of the body from a second surface to an opposite first surface thereof, comprising:
   (a) a chamber-defining member;
   (b) seal means extending around the marginal perimeter of the chamber-defining member for sealably securing the chamber-defining member to the first surface so as to define with said selected area of the first surface of the non-porous steel body a sealed chamber which is impervious to the flow of gas or liquid;
   (c) said chamber defining member being adapted to closely conform to the surface shape of said selected area and to lie in close proximity thereto, said chamber defining member comprising an element which is sufficiently flexible that it deflects toward, and comes to rest upon, the first surface of the body upon evacuation of the chamber so as to reduce and fix the volume of the chamber throughout an optimal operating range;
   (d) means for connecting an evacuating means to the chamber defining member to permit substantial evacuation of the contents of the chamber to establish a partial vacuum therein;
   (e) means for isolating the chamber from the evacuation means after the partial vacuum has been established to maintain the partial vacuum in the chamber so that hydrogen atoms that are generated as a result of corrosion of the second surface of the body and which diffuse through the non-porous material of the body and which exit the first surface within the chamber and which combine to form hydrogen molecules, collect in the chamber thus resulting in a decay of the vacuum in the chamber; and
   (f) vacuum monitoring means for monitoring the decay of the vacuum in the chamber over time to give an indication of the rate of diffusion of hydrogen atoms through the selected area of the non-porous steel body and hence an indication of the rate of corrosion of said second surface.

9. A corrosion monitor as defined in claim 8, wherein the chamber-defining member is constructed of a corrosion resistant material.

10. A corrosion monitor as defined in claim 8 wherein the seal means comprises a surface contact adhesive.

* * * * *